United States Patent [19]

Nikolov et al.

[11] Patent Number: 5,804,426
[45] Date of Patent: Sep. 8, 1998

[54] RECOMBINANT CYCLODEXTRAN GLUCANOTRANSFERASE MUTANTS

[75] Inventors: Zivko L. Nikolov; Hai-Yin Chang, both of Ames, Iowa

[73] Assignee: Iowa State University Research Foundation, Inc., Ames, Iowa

[21] Appl. No.: 696,026

[22] Filed: Aug. 9, 1996

Related U.S. Application Data

[60] Provisional application No. 60/002,110 Sep. 10, 1995.
[51] Int. Cl. $^6$ .............................. C12N 9/10; C12P 19/18
[52] U.S. Cl. ............................................. 435/193; 435/97
[58] Field of Search ....................... 435/193, 97

[56] References Cited

U.S. PATENT DOCUMENTS 5,474,917  12/1995  Schulz et al. ............................. 435/97

OTHER PUBLICATIONS

Bender, H., "Studies of the Mechanism of the Cyclisation Reaction Catalysed by the Wildtype and a Truncated α–Cyclodextrin Glycosyltransferase from Klebsiella pneumoniae Strain M 5 al, and the β–Cyclodextrin Glycosyltransferase from Bacillus cirulans Strain 8", *Carbohydrate Research*, 206, 257–267, (1990).

Evans, R., et al., "Activity and Thermal Stability of Genetically Truncated Forms of *Aspergillus* Glucoamylase", *Gene,* 91, 131–134, (1990).

Fujiwara, S., et al., "Cyclization Characteristics of Cyclodextrin Glucanotransferase are Conferred by the NH$_2$–Terminal Region of the Enzyme", *Applied and Environmental Microbiology,* 58, 4016–4025, (Dec. 1992).

Hellman, J., et al., "Effects of Modifications at the C–terminus of Cyclomaltodextrin Glucanotransferase from *Bacillus cirulans* var. alkalophilus on Catalytic Activity", *Biotechnology and Applied Biochemistry,* 12, 387–396, (1990).

Hofmann, B.E., et al., "Three–dimensional Structure of Cyclodextrin Glycosyltransferase from *Bacillus circulans* at 3.4 Å Resolution", *Journal of Molecular Biology,* 209, 793–800, (1989).

Kaneko, T., et al., "Comparison of CD Composition Produced by Chimeric CGTases", *Agric. Biol. Chem.,* 54, 197–201, (1990).

Kimura, K., et al., "Functions of the COOH–Terminal Region of Cyclodextrin Glucanotransferase of Alkalophilic Bacillus sp. #1011: Relation to Catalyzing Activity and pH Stability", *Biochemical and Biophysical Research Communications,* 161, 1273–1279, (Jun. 1989).

Kitahata, S., "Cyclomaltodextrin Glucanotransferase", *In: Handbook of Amylases and Related Enzymes,* The Amylase Research Society of Japan, ed., Pergamon Press, Tokyo, 154–164, (1988).

Schmid, G., "Cyclodextrin Glycosyltransferase Production; Yield Enhancement by Overexpression of Cloned Genes", *TIBTECH, 7,* 244–248, (Sep. 1989).

Svensson, B., et al., "Sequence Homology Between Putative Raw–starch Binding Domains from Different Starch–degrading Enzymes", *Biochemical Journal,* 264, 309–311, (1989).

Takano, T., et al., "Molecular Cloning, DNA Nucleotide Sequencing, and Expression in *Bacillus subtilis* Cells of the *Bacillus macerans* Cyclodextrin Glucanotransferase Gene", *Journal of Bacteriology,* 166, 1118–1122, (Jun. 1986).

Nakamura et al. (1993) Three Histidine Residues in the Active Center of Cyclodextrin Glucotransferase from Alkophilic Bacillus sp. 1011: Effects of the Replacement on pH Dependence and Transition–State Stabilization, Biochemistry 32: 6624–6631, Jul. 1993.

Fujiwara et al. (1992) Cyclization Characteristics of Cyclodextrin Glucanotransferase Are Conferred by the NH2–Terminal Region of the Enzyme, Applied and Environmental Microbiology, 58 (12): 4016–4025, Dec. 1992.

Yamane et al. (1993) Cyclomaltodextrin, glucanotransferase (CGtase) muteins for enhanced preparation of gamma–cyclodextrin, CAPLUS, CAPLUS ACCES, No. 1993:423687 CAPLUS (119:23687), Feb. 23, 1993.

Yamane et al. (1990) Cyclomaltodextrin glucanotransferase derivatives of Bacillus for improved yield of alpha–cyclodextrin, CAPLUS, CAPLUS ACCESS. No. 1990:153084 CAPLUS (112:153084), Sep. 12, 1988.

Fujiwara et al. (1992) Analysis of Mutations in Cyclodextrin Glucanotransferase from *Bacillus stearothermophilus* Which Affect Cyclization Characteristics and Thermostability, Journal of Bacteriology 174 (22): 7478–7481, Nov. 1992.

*Primary Examiner*—Robert A. Wax
*Assistant Examiner*—Einar Stole
*Attorney, Agent, or Firm*—Schwegman, Lundberg, Woessner & Kluth, P.A.

[57] ABSTRACT

A recombinant cyclodextrin glucanotransferase mutant is provided, which mutant produces lowered amounts of β-cyclodextrins and γ-cyclodextrins compared to wild-type cyclodextrin glucanotransferase.

8 Claims, 8 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear     ( i i ) MOLECULE TYPE: peptide     ( v ) FRAGMENT TYPE: internal     ( x i ) SEQUENCE DESCRIPTION: SEQ ID NO:1:

Ala  Ser  Phe  Asn  Val  Leu
 1                   5

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i i ) MOLECULE TYPE: Genomic DNA     ( x i ) SEQUENCE DESCRIPTION: SEQ ID NO:2:

GTAAAACGAC GGCCAGT                                                          17

( 2 ) INFORMATION FOR SEQ ID NO:3:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear     ( i i ) MOLECULE TYPE: Genomic DNA     ( x i ) SEQUENCE DESCRIPTION: SEQ ID NO:3:

GAGCTCCCGG GTTAGCTAGC CAGTACATTG AAGCTTTTGA A                     41

RECOMBINANT CYCLODEXTRAN GLUCANOTRANSFERASE MUTANTS

This application claims the benefit of U.S. Provisional Application No. 60/002,110, filed on Aug. 10, 1995.

BACKGROUND OF THE INVENTION

Cyclodextrin glucanotransferase (CGTase) is an industrially important enzyme which produces cyclodextrins (CDs) from starch. Cyclodextrins are cyclic oligosaccharides which consist of six, seven, or eight α-1,4-linked D-glucopyranosyl residues. Schmid, G., "Cyclodextrin glycosyltransferase production: yield enhancement by overexpression of cloned genes", *TIBTECH,* 7, 244–248 (1989). CGTase produces cyclodextrins from starch by an intramolecular transglycosylation reaction. Besides the cyclization reaction, CGTase also catalyzes hydrolytic and intermolecular transglycosylation reactions. Kitahata, S. in "Handbook of amylases and related enzymes: Their sources, isolation methods, properties and applications"; (*The amylase research society of Japan,* Ed.); Pergamon Press, Oxford, England; 154–164 (1988). The three-dimensional structure of CGTase from *Bacillus circulans* has revealed that the protein consists of five globular domains, A, B, C, D, and E. Hofmann, B. E., Bender, H. and Schulz, G. E., "Three-dimensional structure of cyclodextrin glycosyltransferase from *Baciullus circulans* at 3.4 Å resolution", *J. Mol. Biol.* 209, 793–800 (1989). Domain E shares 60% amino acid similarity with the raw-starch-binding domain of glucoamylase I and is assumed to be important for the cyclization reaction. Svensson, B., Jespersen, H., Sierks, M. R. & Macgregor, A., "Sequence homology between putative raw-starch binding domains from different starch-degrading enzymes", *Biochem. J.* 264, 309–311 (1989). Previous attempts to show the participation of domain E in the cyclization and/or hydrolysis of starch by using C-terminal deletions and chimeric constructs of CGTases produced contradictory results. Kimura, K., Kataoka, S., Nakamura, A., Takano, T., Kobayashi, S., & Yamane, K., "Functions of the COOH-terminal region of cyclodextrin glucanotransferase of alkalophilic *Bacillus sp.* #1011: relation to catalyzing activity and pH stability", *Biochem. Biophys. Res. Comm.* 161(3), 1273–1279 (1989). Hellman, J., Wahlberg, M., Karp, M., Korpela, T., & Mantsala, P., "Effects of modifications at the C-terminus of cyclomaltodextrin glucanotransferase from *Baciullus circulans* var. alkalophilus on catalytic activity", *Biotechnol. Appl. Biochem.,* 12, 387–396 (1990). Bender, H., "Studies of the mechanism of the cyclization reaction catalyzed by the wild type and a truncated α-cyclodextrin glycosyltransferase from *Klebsiella pneumoniae* strain M5al, and the β-cyclodextrin glycosyltransferase from *Baciullus circulans* strain 8", *Carbohydr. Res,* 206, 257–267 (1990). Fujiwara, S. et al., "Cyclization characteristics of cyclodextrin glucanotransferase are conferred by the NH$_2$-terminal region of the enzyme", *Appl. Environm. Microbiol.,* 58(12), 4016–4025 (1992). Kaneko, T. Kudo, T. & Horikoshi, K., "Comparison of CD composition produced by chimeric CGTases", *Agric. Biol. Chem.,* 54(1) 197–201 (1990).

Thus it is desirable to elucidate the role of domain E on the catalytic behavior of CGTase.

SUMMARY OF THE INVENTION

The present invention provides an altered cyclodextrin glucanotransferase (CGTase) gene which produces an altered cyclodextrin (CD) profile. Preferably, the CGTase gene is altered by the insertion of a heterologous amino acid sequence between domain D and domain E of the wild-type cyclodextrin glucanotransferase. Preferably, the inserted amino acid sequence is , e.g., 6 amino acids long. Most preferably, the amino acid sequence is Ala-Ser-Phe-Asn-Val-Leu (SEQ ID NO: 1). Preferably, the cyclodextrin profile is altered such that an increased amount of at least one cyclodextrin, e.g., α-cyclodextrin or γ-cyclodextrin, is produced compared to the wild-type CGTase. Most preferably, the cyclodextrin profile is altered such that an increased amount of α-cyclodextrin is produced.

The invention further provides an isolated and purified DNA sequence encoding a recombinant cyclodextrin glucanotransferase which produces an altered cyclodextrin profile. Preferably, the CGTase gene is altered by the insertion of a heterologous amino acid sequence between domain D and domain E of the wild-type. Preferably, the heterologous amino acid sequence is Ala-Ser-Phe-Asn-Val-Leu (SEQ ID NO: 1).

Additionally, the invention provides a host cell transformed so as to express the recombinant cyclodextrin glucanotransferase of the present invention.

Also provided is a method of producing an altered or recombinant cyclodextrin glucanotransferase. The method comprises the steps of introducing a recombinant DNA molecule encoding an altered cyclodextrin glucanotransferase into a population of cells; expressing the DNA molecule encoding the cyclodextrin glucanotransferase in the population of cells in an amount sufficient to allow for purification of the cyclodextrin glucanotransferase; and recovering said cyclodextrin glucanotransferase from said cells.

Additionally, the present invention provides a method for altering the production of cyclodextrins obtained from starch upon reaction with cyclodextrin glucanotransferase. The method comprises the step of introducing an expression cassette comprising a recombinant DNA molecule encoding a mutant cyclodextrin glucanotransferase operably linked to a promoter functional in a host cell into the host cell wherein the DNA molecule encodes a cyclodextrin glucanotransferase which produces an altered cyclodextrin profile. Preferably, the cyclodextrin profile is altered such that an increased amount of α-cyclodextrin or γ-cyclodextrin is produced compared to the wild-type CGTase. Most preferably, the cyclodextrin profile is altered such that an increased amount of α-cyclodextrin is produced.

Finally, the present invention provides an expression cassette comprising a gene encoding a recombinant cyclodextrin glucanotransferase which produces an altered cyclodextrin profile operably linked to a promoter functional in a host cell. Preferably, the cyclodextrin glucanotransferase and said promoter sequences are under the transcriptional and translational regulatory control of regulatory regions functional in a host cell. Furthermore, the expression cassette can be used in a method of introducing an exogenous recombinant cyclodextrin glucanotransferase gene into a host cell. The method comprises the steps of first, transforming host cells in vitro with an expression cassette comprising a DNA molecule encoding a mutant cyclodextrin glucanotransferase operably linked to a promoter functional in the host cell. Secondly, the host cells are expanded in vitro and finally, the transformed host cells which express the DNA molecule are identified. Preferably, in this aspect of the invention, the host cell is selected from the group consisting of insect cells, plant cells, prokaryotic cells, diatoms, yeast and algae.

As used herein, the term "heterologous" refers to a DNA sequence or amino acid sequence that either does not occur in the "native" or "wild-type" gene or which is present, but has been moved out of its "native" or "wild-type" position.

BRIEF DESCRIPTION OF THE FIGURES

FIG. 7(*a*) depicts the production of α-, β-, and γ-CDs from soluble starch by wild-type CGTases.

FIG. 7(*b*) depicts the production of α-, β-, and γ-CDs from soluble starch by modified CGTases.

DETAILED DESCRIPTION OF THE INVENTION

To elucidate the role of domain E on the catalytic behavior of a *B. macerans* CGTase, three new constructs have been made. The first construct, truncated CGTase, contained no domain E. The second construct, chimeric CGTase, contained the raw-starch-binding domain (SBD) of glucoamylase I (GAI) of *Aspergillus niger* instead of domain E. The last construct, modified CGTase, was made by inserting six amino acids in CGTase gene.

The invention will be further described by reference to the following detailed examples, wherein *E. coli* strains JM105 (Pharmacia), XL1BLUE (Stratagene) and Novablue (Novagen) were used for general DNA manipulation. *E. coli* strain JM105 was used for the production of cyclodextrin glucanotransferase (CGTase). Plasmid pREI contains 2.1 Kb glucoamylase I (GAI) gene from *A. niger* in pBS+ vector (Stratagene). Evans, R., Ford, C., Sierks, M., Nikolov, Z. and Svensson, B., "Activity and thermal stability of genetically truncated forms of *Aspergillus* glucoamylase", Gene, 91, 131–134 (1990). Plasmid pLCGT1, containing 2.3 Kb CGTase gene of *B. macerans* in pCRII vector (Invitrogen), was obtained from Dr. B. Tao of Purdue University. The sequence of CGTase gene was described by Takano et al., "Molecular cloning, DNA nucleotide sequencing, and expression in *Bacillus subtilis* cells of the *Bacillus macerans* cyclodextrin glucanotransferase gene", *J. Bacteriol.*, 166(3), 1118–1122 (1986). The pT7Blue T-vector for cloning of PCR products was purchased from Novagen. The pKK223-3 vector for overexpression of CGTase in *E. coli* was purchased from Pharmacia.

General DNA manipulation was done by the standard methods described in Maniatis et al., "Molecular Cloning: A Laboratory Manual", Cold Spring Harbor Laboratory, New York, 1989. *E. coli* was transformed using $CaCl_2$ or electroporation according to Aubusel et al., Current protocols in molecular biology, 1987. Small and large scale plasmid preparations were performed using Wizard Minipreps and Qiagen-tip purchased from Promega and Qiagen. Restriction endonuclease, ligase and Taq polymerase were purchased from Promega. Alkaline phosphatase and Klenow fragment were purchased from Pharmacia, whereas Geneclean kit was purchased from Bio101.

The LB-amp plate (75 μg/ml ampicillin, 1.5% agar, 1% trypton, 0.5% yeast extract, and 0.5% NaCl, $pH_{7.2}$) was used for the selection of *E. coli* transformants. The X-gal-IPTG plate (LB agar plates containing 50 μg/ml ampicillin, 15 μg/ml tetracycline, 70 μg/ml X-gal, and 80 μM IPTG) was used for screening of PCR recombinants. The LB-amp-starch plate (LB-amp agar plates containing 1% soluble starch) was used for plate-enzyme assays to detect the starch-hydrolyzing activity of CGTase. LB-amp medium was used to cultivate *E. coli* cells for enzyme purification.

EXAMPLE 1

Construction and manipulation of CGTase genes

Figure 1:
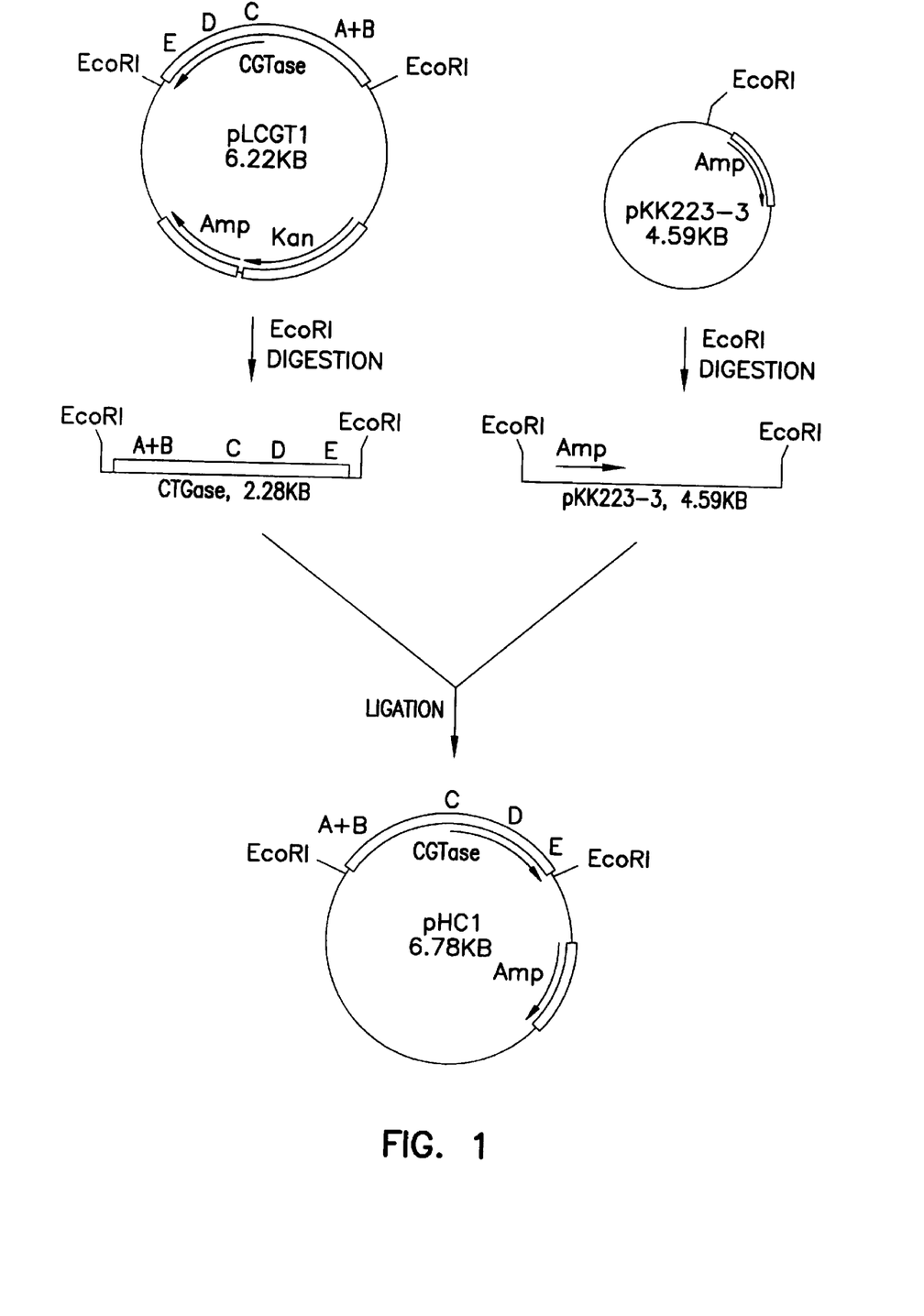
FIG. 1 is a depiction of the construction of plasmid pHC1.
Figure 2:
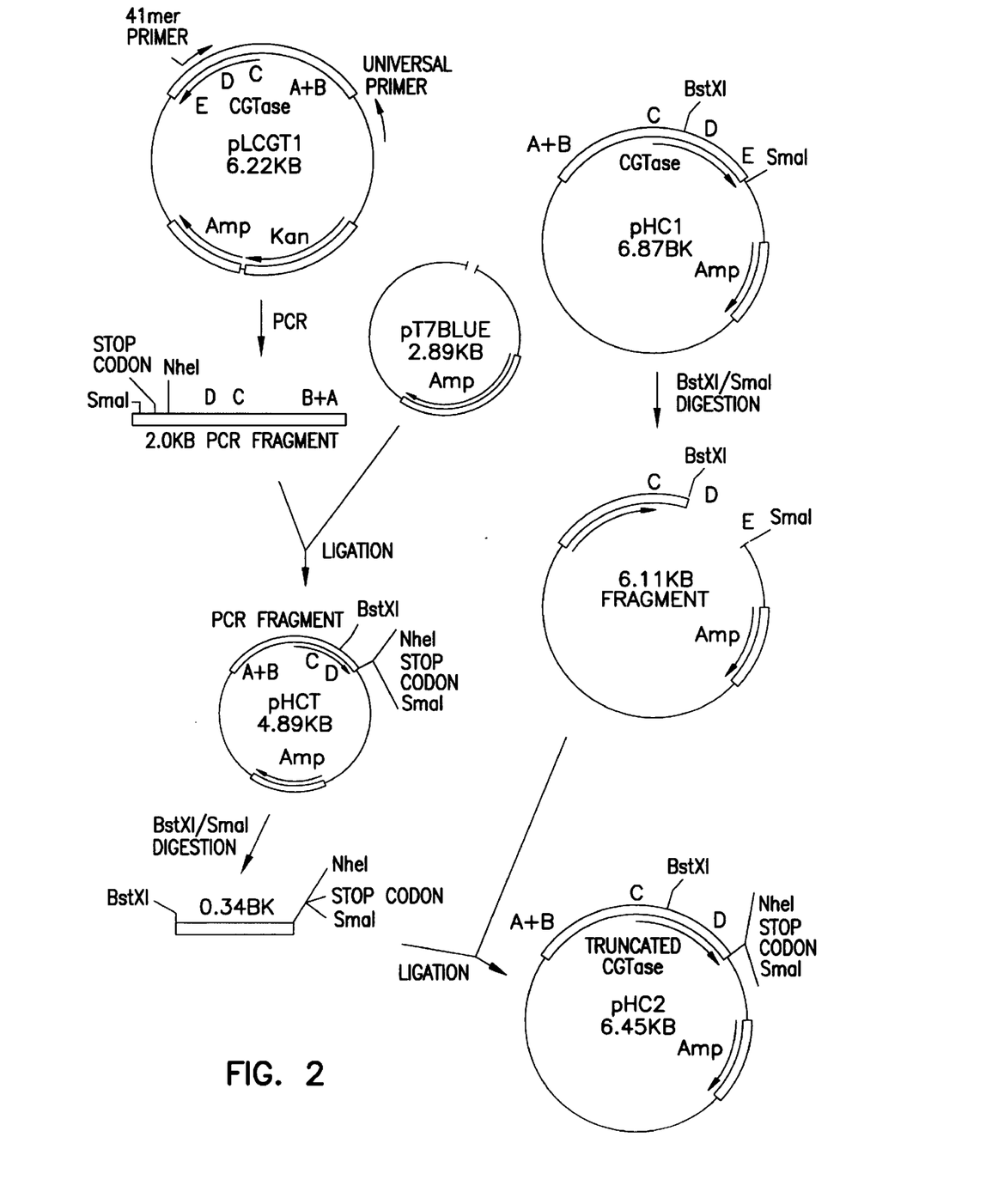
FIG. 2 is a depiction of the construction of plasmid pHC2.

To construct a plasmid for overexpression of *B. macerans* CGTase gene in *E. coli*, an EcoRI DNA fragment (2.28 kb) containing CGTase gene from plasmid pLCGT1 was subcloned into pKK223-3 to form plasmid pHC1 (FIG. 1). To construct CGTase with deletion of domain E (Thr584-Asn687), a universal primer and a 41-mer were used to amplify the CGTase gene in pLCGT1 by polymerase chain reaction (PCR). The primers were synthesized by Nucleic Acid Facility of Iowa State University and DNA International Inc.. The universal primer was 5'GTAAAACGACG-GCCAGT 3'(SEQ ID NO: 2); the 41-mer primer was 5'GAGCTCCCGGGTTAGCTAGCCAGTACAT-TGAAGCTTTTGAA 3'(SEQ ID NO: 3). The 41-mer primer matches the DNA sequence encoding the region between domains D and E of CGTase (Phe577-Leu583). Therefore, the PCR product was about 2.0 kb and encoded domains A through D. Due to the design of the 41-mer primer sequence, a NheI restriction site, a stop codon and a SmaI restriction site were generated at the 3' end (corresponding to Leu583) of the PCR fragment. The 2.0 kb PCR fragment was then cloned into pT7Blue T-vector (Novagen), and designated as pHCT. To create an expression plasmid for truncated CGTase gene, plasmid pHC1 DNA was digested with BstXI and SmaI. The large fragment (6.11 kb) containing pKK223-3 vector and part of CGTase gene (corresponding to Ser1-Ile470) was ligated with the 0.34 kb BstXI-SmaI DNA fragment (corresponding to Thr471-Leu583) of 2.0 kb PCR fragment from pHCT to construct plasmid pHC2. The plasmid pHC2 contains pKK223-3 vector, part of CGTase gene encoding domains A to D, and NheI site and stop codon at the 3'-end of this truncated CGTase gene (FIG. 2). The NheI site in pHC2 was used as a convenient restriction site for further constructing chimeric and modified CGTases.

Figure 3:
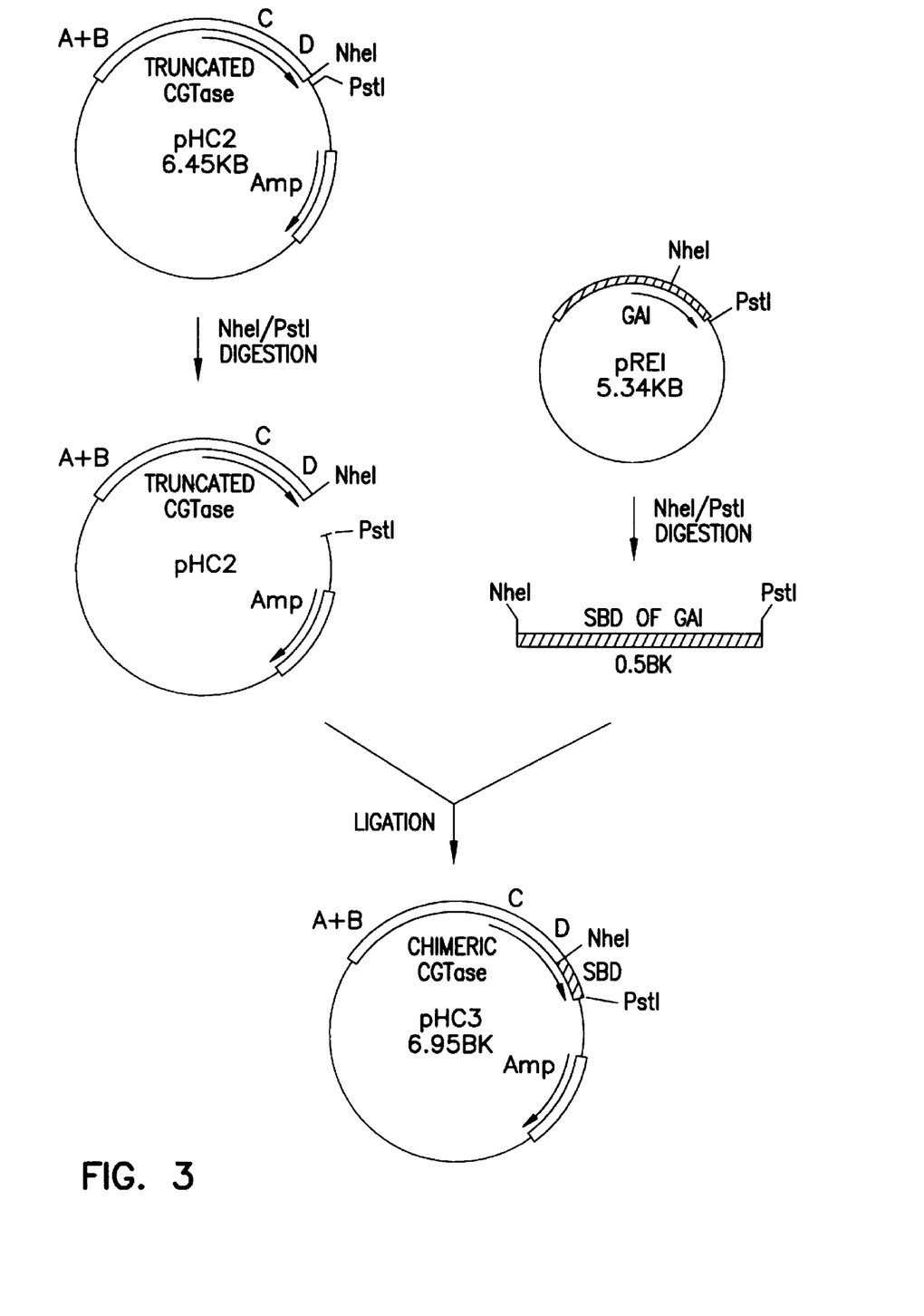
FIG. 3 is a depiction of the construction of plasmid pHC3.

To create a chimeric CGTase, a NheI-PstI fragment (0.5 kb) from plasmid pREI, containing the sequence of the starch-binding-domain of GAI, was inserted into NheI-PstI sites of plasmid pHC2. The resulting plasmid was named pHC3 (FIG. 3).

Figure 4:
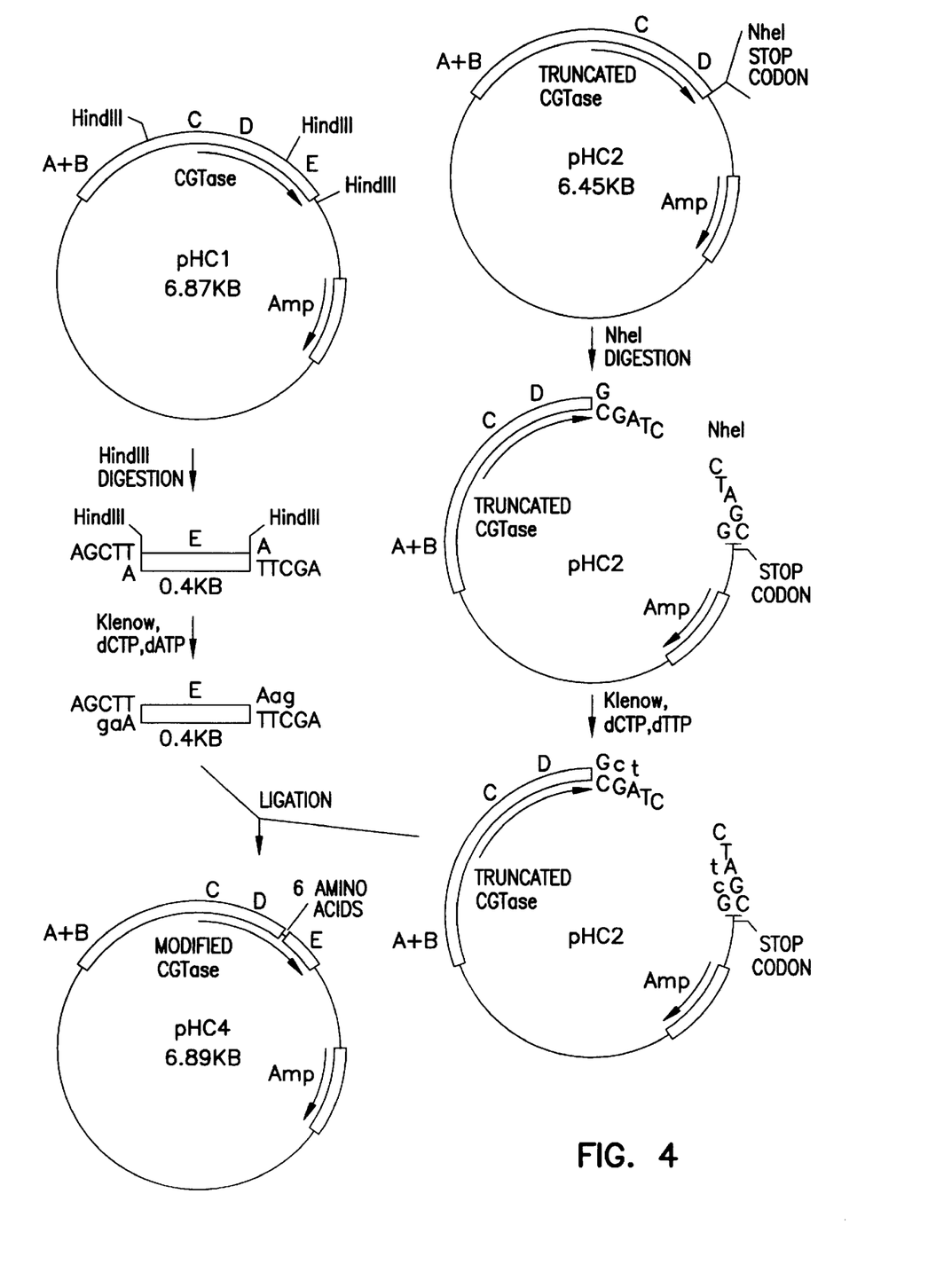
FIG. 4 is a depiction of the construction of plasmid pHC4.

A modified CGTase with six-amino-acid insertion between domain D and E was constructed as follows. A 0.4 kb HindIII fragment was isolated from pHC1 and the cohesive ends of this HindIII fragment were partially filled in with dGTP and dATP. The modified 0.4 kb HindIII fragment from pHC1 encoded domain E, five amino acids (Ser579-Leu583) of domain D, and one amino acid (Ala) derived from the modification of 5'-end of HindIII fragment. Plasmid pHC2 DNA was digested with NheI and subsequently partially filled in with dCTP and dTTP to be compatible with the above modified HindIII ends. The modified pHC1 HindIII fragment was inserted into the modified NheI site of pHC2 to create pHC4 (FIG. 4).

Figure 5:
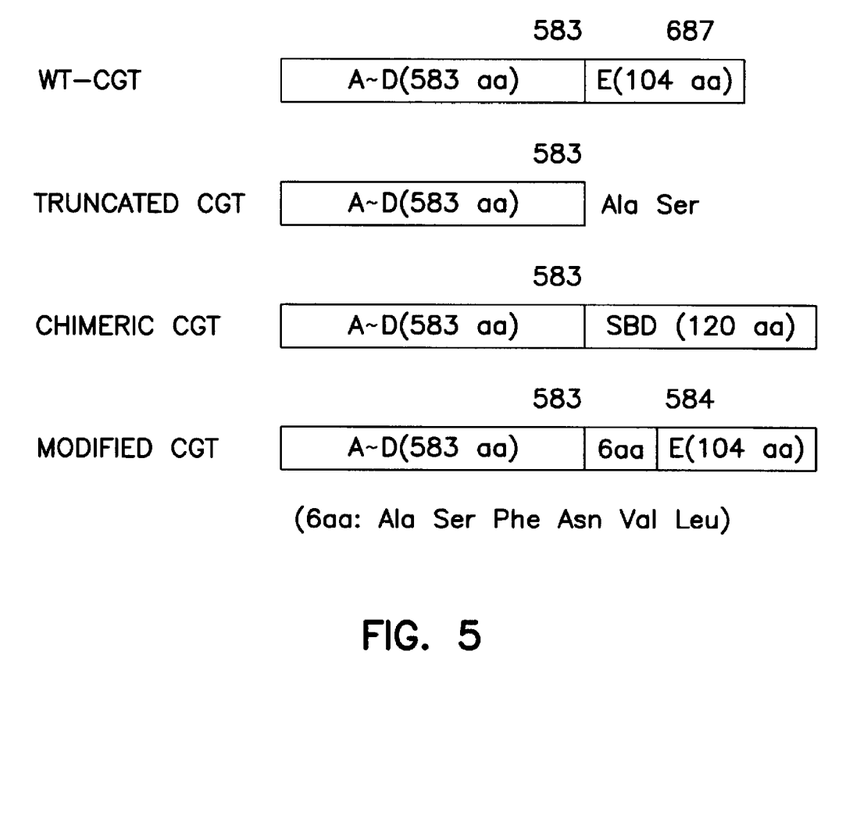
FIG. 5 is a schematic representation of CGTase constructs. Abbreviations: WT, wild-type; CGT, cyclodextrin glucanotransferase; SBD, starch-binding-domain of glucoamylase I.

DNA sequencing was done by the NAF of ISU to confirm that the DNA sequences of pHC1, pHC2, pHC3 and pHC4 were correct. The domain organization of CGTase constructs are shown in FIG. 5.

EXAMPLE 2
Production and purification of CGTases

E. coli JM105 cells containing pHC1, pHC2, pHC3, or pHC4 were grown in 1 liter of LB-amp medium at 37° C. The expression of CGTases was induced with 0.3 mM IPTG added at $A_{600}$ of 0.6. After the induction, the cells were incubated at 37° C. for 3 hours. Cells were harvested by centrifugation (5,000 xg, for 10 minutes), and then broken in two passes by a French Press at a pressure of 4,000 psi. The soluble crude enzyme was separated from the cell debris by centrifugation (10,000 xg, for 10 minutes). Ammnonium sulfate (80% saturation) was added to the supernatant and the solution was stirred at 4° C. for 1 hour. After centrifugation (16,000 xg, for 30 minutes), the precipitate was dissolved in 10 ml of 20 mM Tris buffer, pH 7.5. The enzyme solution was dialyzed and applied to α-CD-coupled Sepharose 6B column. The various constructs were eluted with 15 mM α-CD. The affinity gel was prepared according to the method described by Laszlo at al., "Purification of cyclodextrin glycosyltransferase enzyme by affinity chromatography", Starch/Starke, 33, 281–283 (1981). The epoxy-activated Sepharose 6B was purchased from Pharmacia.

Figure 6:
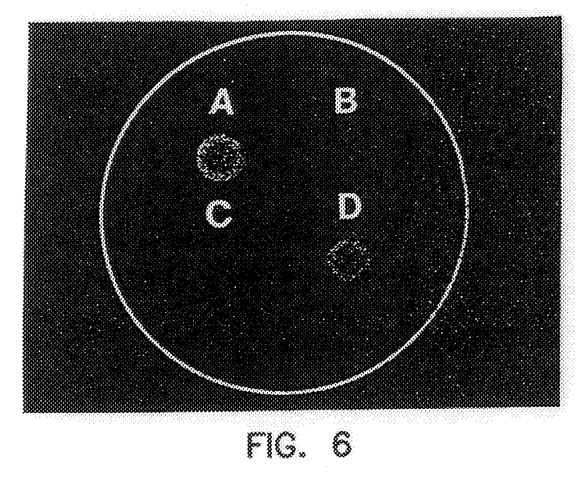
FIG. 6 is a depiction of the halos formed by *E. coli* transformants on a starch-plate. Each transformant was plated onto a LB-amp-starch plate (1% starch) and incubated overnight at 37° C. After incubation, the plate was exposed to $I_2$ vapor to examine the formation of halos. (A) *E. coli* JM105 carrying pHC1 (wild-type CGTase); (B) *E. coli* JM105 carrying pHC2 (truncated CGTase); (C) *E. coli* JM105 carrying pHC3 (chimeric CGTase); (D) *E. coli* JM105 carrying pHC4 (modified CGTase).

Starch-plate assay was used to confirm the expression of the wild-type and engineered CGTases in E. coli. E. coli JM105 carrying pHC1, pHC2, pHC3 or pHC4 was plated on a LB-amp-starch plate (1% starch) and incubated overnight at 37° C. The formation of halos was examined by exposing the plate to $I_2$ vapor. The halos which appeared around colonies indicate that starch has been degraded by the hydrolytic activity of CGTases. E. coli JM105 carrying pHC1, which has the wild-type CGTase gene, showed a large halo and served as a positive control (FIG. 6). E. coli JM105 carrying pHC4, which has the modified CGTase gene, also formed a large halo. These results indicated that the wild-type and modified CGTases were produced in E. coli and had the starch-hydrolizing activity.

No halos were detected around the colonies of E. coli JM105 carrying pHC2 or pHC3, indicating that no active truncated CGTase (pHC2) and chimeric CGTase (pHC3) were produced in E. coli.

Wild-type CGTase, truncated CGTase, chimeric CGTase and modified CGTase were purified from E. coli as described above. Purified wild-type CGTase showed a single band (74 kDa) on the SDS-PAGE and Western blot. Modified CGTase showed one major band of 74 kDa and several bands with molecular weights between 40–50 kDa (data not shown). The chimeric CGTase was purified and the existence of the starch-binding-domain (SBD) of GAI was confirmed by Western blotting using anti-glucoamylase I. A proteolytic degradation was also observed for chimeric CGTase. The purification and subsequent detection of truncated CGTase was unsuccessful.

EXAMPLE 3
Analytical assays

α-CD activity of CGTase was assayed by using the methylorange method described by Lejeune et al., "A spectrophotometric assay for the cyclization activity of cyclomaltohexaose (α-cyclodextrin) glucanotransferase", Analyt. Biochem., 181, 6–11 (1989). The enzyme reaction was performed at 40° C. The reaction mixture contained 1% soluble starch, 35 μM methylorange in 50 mM phosphate buffer, pH 6.0. To stop the reaction, 6M HCl was added to a final concentration of 0.3M. The reaction solution was incubated at 16° C. for 30 min, and the absorbance at 505 nm was measured. One unit of cyclization activity is defined as the amount of enzyme that catalyzes the formation of 1 μmole α-CD per minute under the assay conditions.

The specific activity of the modified CGTase was reduced to 3.3% of that of the wild-type CGTase (Table 1). The cyclization and hydrolytic activities of the truncated CGTase were not detectable. The chimeric CGTase showed no cyclization activity and very weak hydrolytic activity, which was difficult to quantify. The latter results suggest that the domain E of CGTase is important for cyclization activity.

The attachment of SBD to the C-terminus of truncated CGTase did not produce CD-functional enzyme.

TABLE 1

| α-CD specific activity of wild-type and engineered CGTases. | |
|---|---|
| Enzyme | Specific activity (U/mg) |
| WT-CGT | 211 |
| Truncated CGT | not detectable |
| Chimeric CGT | not detectable |
| Modified CGT | 7 |

The amounts of α-, β-, and γ-CDs produced from soluble starch by wild-type and modified CGTases were assayed by HPLC. Specifically, a reaction mixture (pH 6.0) containing 5% soluble starch, 3 mM $CaCl_2$, and 50 mM phosphate buffer was incubated with 0.9 U of each the wild type and the modified CGTase in a total volume of 5 ml at 40° C. Samples were withdrawn and heated in a boiling water bath for 10 minutes to stop the reaction. The concentration of α-, β-, and γ-CD in the reaction mixture was measured by HPLC on a Spherisorb-$NH_2$ column (Phase Separations Inc, Norwalk, Conn.) equipped with a RI detector (Erma RI detector, ERC-7512, Erma Inc). The mobile phase was 65% aqueous acetonitrile at a flow rate of 1 ml/min.

Figure 7A:
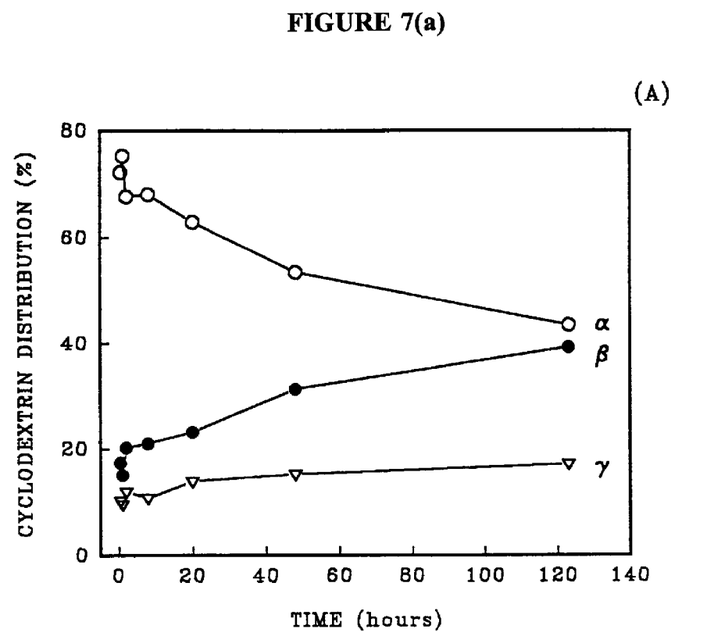
Figure 7B:
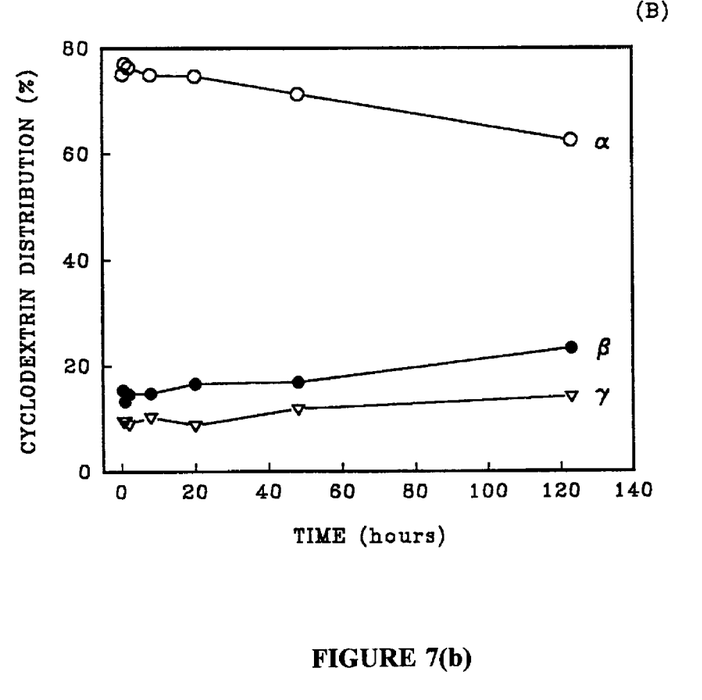

Time course of CD production by CGTases is shown in FIG. 7. Wild-type CGTase produced mainly α-CD at the initial stage of the reaction (FIG. 7A). The α-CD production gradually decreased with the progression of the reaction. The amount of β-CD increased with the increase of the reaction time. The product profile of modified CGTase showed significant difference from wild-type CGTase (FIG. 7B). The modified CGTase produced significantly lower amounts of β- and γ-CDs than the native enzyme, while maintaining the same level of α-CD production. The productivities of β-CD and γ-CD were low, and did not change even after prolonged incubation. These results indicate that the special modification of CGTase changed the product profile of the enzyme.

Figure 8:
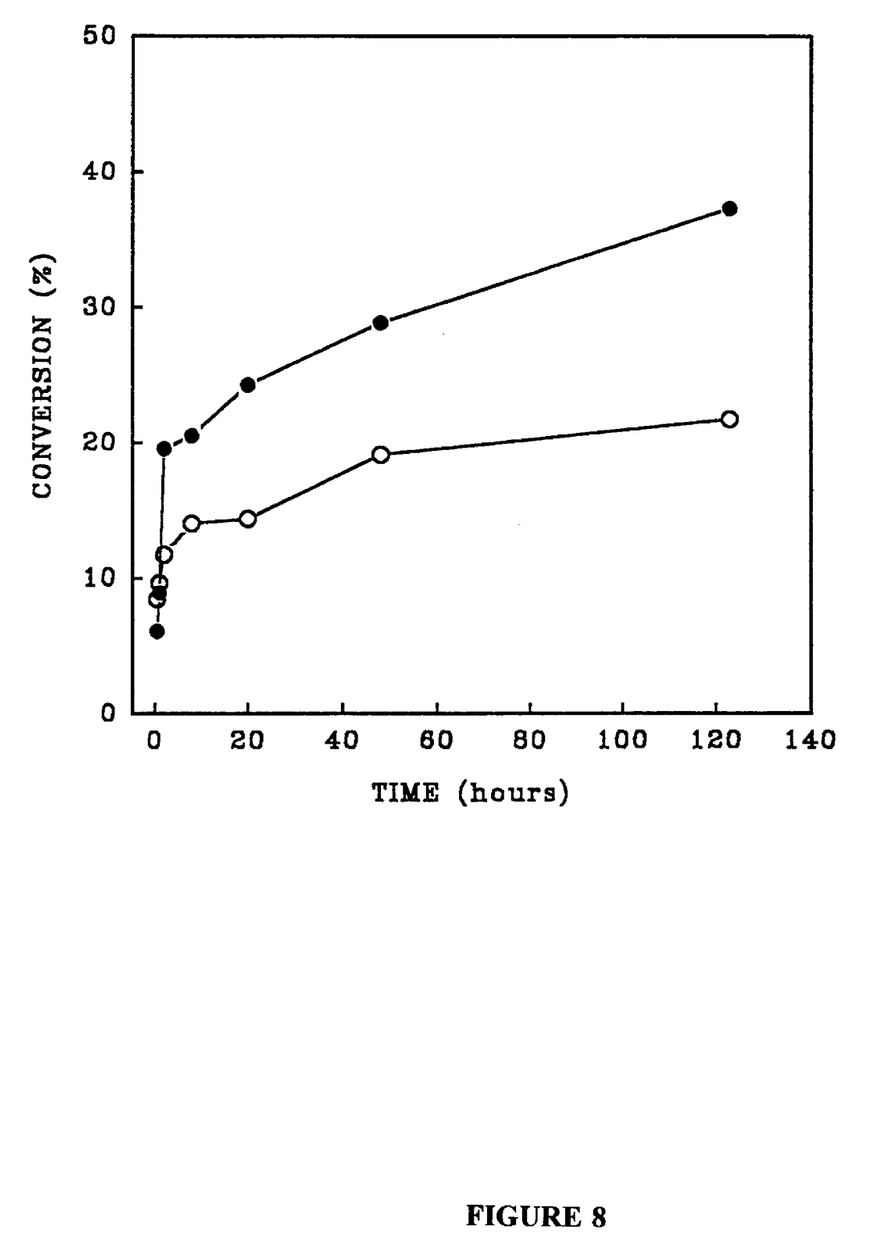
FIG. 8 is a graphical depiction of the degree of total cyclodextrin conversion from 5% starch by wild-type (●) and modified CGTases (○).

The degree of total CD conversion from 5% starch is shown in FIG. 8. The modified CGTase has lower conversion compared to wild-type CGTase mainly due to the reduced β-CD production.

The protein concentration was determined using the Bio-Rad protein assay. Sodium dodecyl sulfate (SDS)- polyacrylamide gel electrophoresis (PAGE) was performed on 8.5% gels and protein bands were stained with Coomassie Brilliant blue. The Western blot was performed by transferring the proteins from the SDS-PAGE gels to a nitrocellulose membrane with a Transblot SD semidry-blotter (Bio-Rad). Polyclonal antibodies against CGTase were used to detect the presence of CGTases.

What is claimed is:

1. An recombinant altered wild-type cyclodextrin glucanotransferase comprising a heterologous amino acid sequence inserted between domain D and domain E.

2. The recombinant altered cyclodextrin glucanotransferase of claim 1 wherein the cyclodextrin profile is altered such that an increased amount of at least one cyclodextrin is produced compared to the wild-type cyclodextrin glucanotransferase.

3. The recombinant altered cyclodextrin glucanotransferase of claim 2 wherein the cyclodextrin profile is altered such that an increased amount of α-cyclodextrin is produced compared to the wild-type cyclodextrin glucanotransferase.

4. The recombinant altered cyclodextrin glucanotransferase of claim 2 wherein the cyclodextrin profile is altered such that an increased amount of γ-cyclodextrin is produced compared to the wild-type cyclodextrin glucanotransferase.

5. The recombinant altered cyclodextrin glucanotransferase of claim 1 wherein the heterologous amino acid sequence comprises SEQ ID NO: 1.

6. The recombinant altered cyclodextrin glucanotransferase of claim 1 wherein the cyclodextrin profile is altered such that a decreased amount of β- and γ-cyclodextrin is produced compared to the wild-type cyclodextrin glucanotransferase.

7. The recombinant altered cyclodextrin glucanotransferase of claim 1 wherein the cyclodextrin profile is altered such that an increased amount of at least one cyclodextrin is produced compared to the wild-type cyclodextrin glucanotransferase, and wherein the cyclodextrin profile is altered such that a decreased amount of β- and γ-cyclodextrin is produced compared to the wild-type cyclodextrin glucanotransferase.

8. The recombinant altered cyclodextrin glucanotransferase of claim 7 wherein the cyclodextrin profile is altered such that an increased amount of α-cyclodextrin is produced compared to the wild-type cyclodextrin glucanotransferase and wherein the cyclodextrin profile is altered such that a decreased amount of β-cyclodextrin is produced compared to the wild-type cyclodextrin glucanotransferase.

* * * * *